United States Patent
Rhodes et al.

(10) Patent No.: US 7,257,496 B2
(45) Date of Patent: Aug. 14, 2007

(54) METHOD AND APPARATUS FOR MONITORING SF6 GAS AND ELECTRIC UTILITY APPARATUS

(75) Inventors: George W. Rhodes, Corrales, NM (US); Albert Migliori, Santa Fe, NM (US); Tristan Fin, Albuquerque, NM (US); Steven Frank Willard, Albuquerque, NM (US)

(73) Assignee: Avistar, Inc., Albuquerque, NM (US)

( * ) Notice: Subject to any disclaimer, the term of this patent is extended or adjusted under 35 U.S.C. 154(b) by 15 days.

(21) Appl. No.: 11/335,569

(22) Filed: Jan. 20, 2006

(65) Prior Publication Data

US 2007/0027640 A1    Feb. 1, 2007

Related U.S. Application Data

(60) Provisional application No. 60/713,366, filed on Sep. 2, 2005, provisional application No. 60/702,999, filed on Jul. 28, 2005.

(51) Int. Cl.
*G01F 17/00* (2006.01)
(52) U.S. Cl. .................................................. 702/51
(58) Field of Classification Search ............... 702/51
See application file for complete search history.

(56) References Cited

U.S. PATENT DOCUMENTS

| | | | |
|---|---|---|---|
| 4,489,592 A | 12/1984 | Pacanowski et al. | |
| 4,802,370 A | 2/1989 | EerNisse et al. | |
| 5,388,451 A * | 2/1995 | Stendin et al. | 73/438 |
| 5,693,873 A | 12/1997 | Thuries et al. | |
| 6,205,846 B1 * | 3/2001 | Dupraz et al. | 73/40 |
| 6,263,914 B1 | 7/2001 | Meyer et al. | |
| 6,651,483 B1 * | 11/2003 | Meyer et al. | 73/23.28 |

* cited by examiner

*Primary Examiner*—John Barlow
*Assistant Examiner*—Demetrius R. Pretlow
(74) *Attorney, Agent, or Firm*—Snider & Associates; Ronald R. Snider

(57) ABSTRACT

A method for detecting loss of SF6 gas from electrical utility apparatus determines a molar ratio of gas in a container at an initial time and of gas in the container at a subsequent time. Measurement of temperature is determined by averaging ambient temperature and temperature of the surface of the container. The initial values of pressure and temperature define the initial value of n as follows:

$$n_o = P_{gas\,o} / T_{gas\,o}$$

The value at a subsequent time is $$n_n = P_{gas\,n} / T_{gas\,n}$$

The molar ratio can be defined as $$n_n/n_o \text{ or as } n_o/n_n.$$

18 Claims, 3 Drawing Sheets

METHOD AND APPARATUS FOR MONITORING SF6 GAS AND ELECTRIC UTILITY APPARATUS

RELATED APPLICATIONS

This application is a continuation in part of Provisional Application 60/702,999 filed Jul. 7, 2005 and a continuation in part of Provisional Application 60/713,366 filed Sep. 2, 2005.

FIELD OF THE INVENTION

This invention relates generally to SF6 monitoring of containers or tanks for electrical apparatus used in power transmission. More particularly the invention relates to monitoring of SF6 gas in a tank containing electrical switching components.

BACKGROUND OF THE INVENTION

High voltage circuit breakers are used in the transmission and distribution of electrical energy. These circuit breakers are located inside of tanks which contain SF6 gas. The SF6 gas acts as an electrically insulating gas to prevent arcing. The purpose of the gas is to control arcing across electrical contacts during opening of closing of contacts in the breaker.

SF6 gas monitors are known in the art as shown in U.S. Pat. No. 4,489,592 Pacanowski et al., U.S. Pat. No. 4,802,370 EerNisse et al., U.S. Pat. No. 5,388,451 Stendin et al., U.S. Pat. No. 6,263,914 Meyer et al., and U.S. Pat. No. 6,651,483 Meyer et al. In the above referenced patents, SF6 density in a container which houses electrical switch gear is monitored by observing density and comparing the measurement to an industry standard. Monitoring of density change necessarily involves computations of the quantity of gas present in the container. The quantity of gas present in the container is determined by measuring gas pressure and gas temperature and applying the perfect gas equation.

$$PV=nRT$$

In the prior art, the temperature inside of the electrical apparatus container has been measured from the outside. Measurement from the outside is necessary when a temperature measuring transducer is not incorporated in the container at the time of manufacture. Because of arcing considerations, and conditions inside the container, it is generally impractical to measure temperature of the gas directly inside of the container, especially in the case where it is desired to provide SF6 monitoring on an existing tank which does not include a provision for temperature measurement inside the tank. For this reason, the prior art measures temperature of the tank skin, and attempts to estimate the true temperature inside the tank in order to as closely as possible estimate the true temperature of the gas inside the tank.

In the prior art devices, measurements are made only at specific times, and information relating to density loss as a function of time or trends of density loss are not made.

Daily variations of SF6 pressure due to temperature change, preclude using pressure measurements alone in detecting smaller leaks. The ideal gas law is used to adjust for pressure measurements alone. Under the ideal gas law, the ideal pressure temperature relationship of SF6 is linear.

In electric utilities, several hundred thousand pounds of SF6 per year are lost due to faulty seals. The loss of this expensive dielectric gas is an environmental concern and is subject to routine pressure inspections to determine leakage. Since SF6 is a potent greenhouse gas, early detection of leaks can prevent environmental degradation, reduce replacement costs and allow maintenance staff to implement repair before an emergency condition develops. Slow leaks from mechanical seals are difficult to detect and current technology in the electrical industries lack the requisite sensitivity.

BRIEF SUMMARY OF THE INVENTION

This invention uses the pressure and a calculated temperature of SF6 gas and calculates the number of moles present and corrects for changes in ambient condition in both the gas and its container. The number of moles n present in a fixed volume V is also a direct function of the pressure P and the temperature T of the gas. In this invention, there is collection of data and performance of a running calculation using a least squares fitting routine which is used to determine changes in molar content of the container. If the slope of the change of the molar content changes by a predetermined value, it is determined that a leak must be present. An alarm is then signaled electronically to an operator who monitors leak conditions when the predetermined value is exceeded. The trend average leak calculation allows for efficient forecasting for maintenance activities in the presence of slow SF6 leaks.

This invention utilizes two enclosures housing electronic circuitry. The first enclosure provides for analog to digital conversion, memory and input and output signal interfaces. The second enclosure provides for input and output signal interfaces, memory for retaining data until downloaded, a microprocessor for computing molar ratios and ratio trendlines using historical and recent data.

The temperature sensor housing mounts on a circuit breaker housing whose pressure is being monitored. The tank temperature sensor has insulation exterior of the tank in order to hold the tank temperature sensor close to the temperature of the tank and insulate the temperature sensor from the ambient conditions. There is also a separate ambient temperature sensor located on the outside of the insulation that insulates the tank sensor. The separate ambient temperature may also be located at a location remote from the temperature sensor transducer and remote from the tank. There are leads from each temperature sensor extending to the electronic enclosure which includes analog to digital conversion circuits.

One function of the microprocessor is to calculate a molar ratio by comparing the initial number of calculated moles of SF6 upon sensor activation to the current number of calculated moles using the ideal gas equation:

$$PV=nRT$$

where:

$$n=PV/RT$$

However since the volume V and R (the universal gas constant) are constant, the relationship n is proportional to P/T applies. The initial values of pressure and temperature define the initial value of n as follows:

$$n_o = P_{gas\ o}/T_{gas\ o}$$

The value at a subsequent time is $$n_n = P_{gas\ n}/T_{gas\ n}$$

The molar ratio can be defined as $$n_n/n_o \text{ or as } n_o/n_n$$

It is preferable to use $n_n/n_o$ because this gives a value which decreases upon loss of atoms from the container. The slope of a line fit to a data set using this ratio would be negative in the instance of an SF6 leak. FIG. 3 shows data taken with a molar ratio definition where the loss is seen as the negative slope of the leaking mole ratio. However the ratio $n_o/n_n$ can be used and the resultant calculation will be an increasing value. The slope of the increasing value can also be used to determine leaking mole ratio.

The microprocessor also generates a leak trend alarm if the sum of a least squares analysis of the calculated molar ratio show shows a slope equivalent to a leak rate of 0.2 kg/yr.

Determination of the temperature $$T_{gas}$$

as used in this invention is performed by measuring the ambient temperature and the temperature of the outer surface (skin) of the container and computing an average of the two temperatures as follows:

$$(T_{ambient}+T_{surface})/2$$

A method for detecting loss of SF6 gas from electric utility apparatus comprises the steps of: taking measurements at a beginning time and a later time, wherein taking measurements comprise the steps of; detecting pressure of a gas containing SF6 in a container which encloses an electric utility apparatus, detecting ambient temperature where the electric utility apparatus is located, detecting temperature of an outer surface of the container, computing an average of the ambient temperature and the temperature of an outer surface of the container, computing a molar ratio using pressure and the computed average temperature measurements taken at the beginning time and the later time, and wherein loss is determined by comparing molar ratio between measurements taken at the beginning time and the later time.

The method for detecting loss of SF6 gas from electric utility apparatus determines the molar ratio as follows:

$$\text{molar ratio}=n_n/n_o$$

or $$\text{molar ratio}=n_o/n_n$$

where $n_n$ is a measurement taken at a subsequent time and $n_o$ is a measurement taken at the beginning time.

The method for detecting loss of SF6 gas from electric utility apparatus also comprises the steps of taking a plurality of measurements at different times after the beginning time and establishing a ratio trend line based upon at least two of the plurality of measurements.

DETAILED DESCRIPTION OF THE PREFERRED EMBODIMENT

Figure 1:
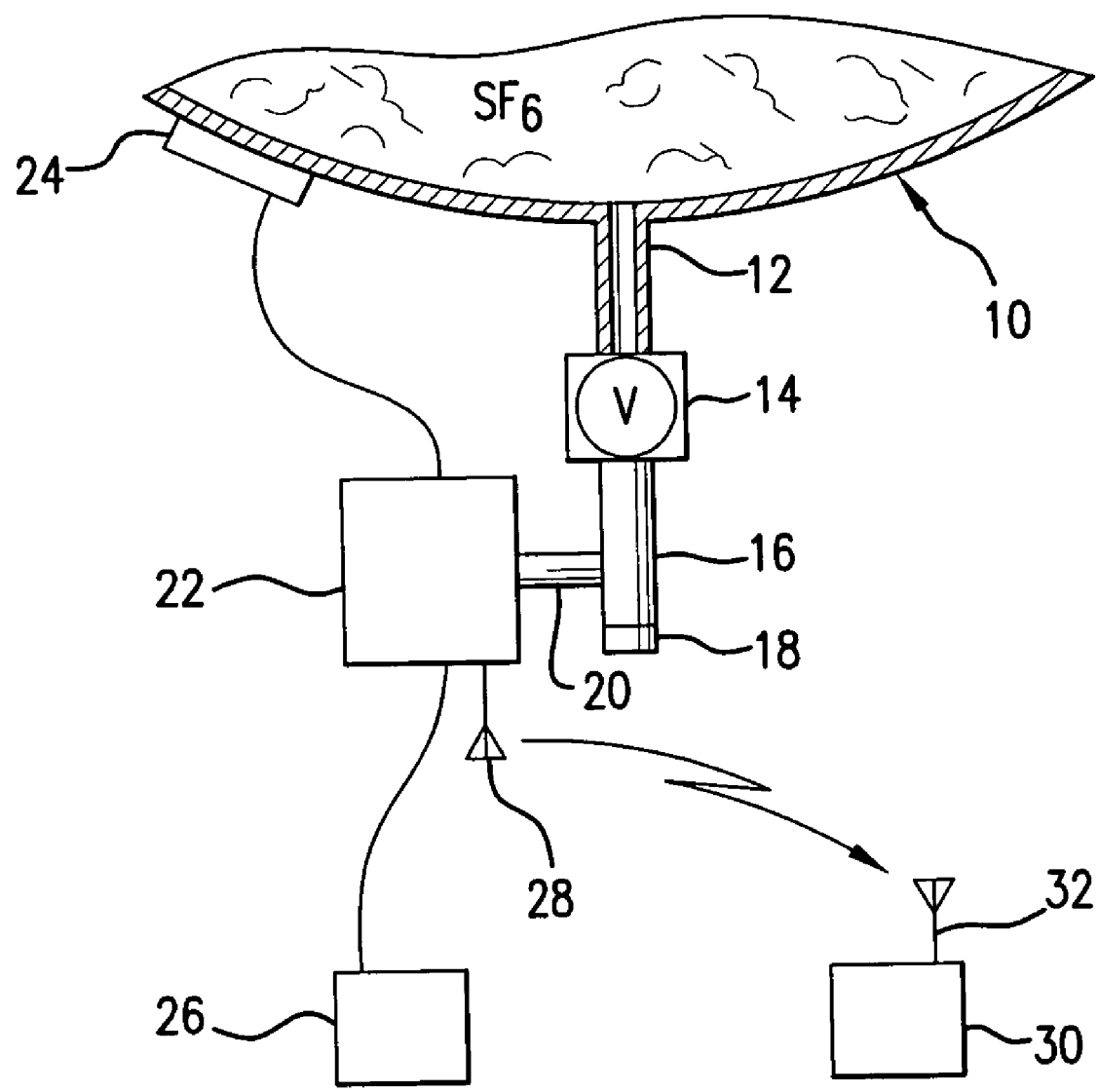
FIG. 1 shows a circuit breaker container and monitoring equipment.

FIG. 1 shows a container (10) containing SF6 gas. Attached to the container is a service port (12) which is connected to a service valve (14). Service valve (14) is connected to a "T" pipe fitting (16). One end of the "T" pipe fitting (16) has a cap (18). Connected to the "T" fitting (16) is a nipple (20) which connects to a detector (22). The detector (22) also contains a radio board which sends unprocessed data to the gateway (30) by way of the transmitting antenna (28) and receiving antenna (32). The processor (computer) is contained in the gateway (30). Gateway (30) is a receiver, microprocessor (computer) and internet link located at a utility substation where a plurality of SF6 sensors are located. The microprocessor and associated memory collect data from all sensors located in the utility substation through antenna (32) and provide this data to the internet communication link for transmittal to a central monitoring location. The utility substation is normally not continuously manned and is therefore monitored from a remote location by use of the gateway (30). The electronic circuitry is connected to a pressure transducer located within the detector (22) which is in fluidic communication with gas in the container (10) when valve (14) is open. The detector is also connected to a temperature sensor (24) which is placed against the tank (10) and which is insulated on its exterior in order to maintain the temperature sensor at a level which is close to the skin temperature of the container (10). The detector (22) is also connected to an ambient air temperature sensor (26). As shown in FIG. (1), the ambient air temperature (26) is located remotely from the tank (10). However, the ambient air temperature sensor may be located on the exterior of the body of the tank temperature detector (24) in a manner wherein the ambient air temperature sensor is in contact with the air and insulated from the tank.

Figure 2:
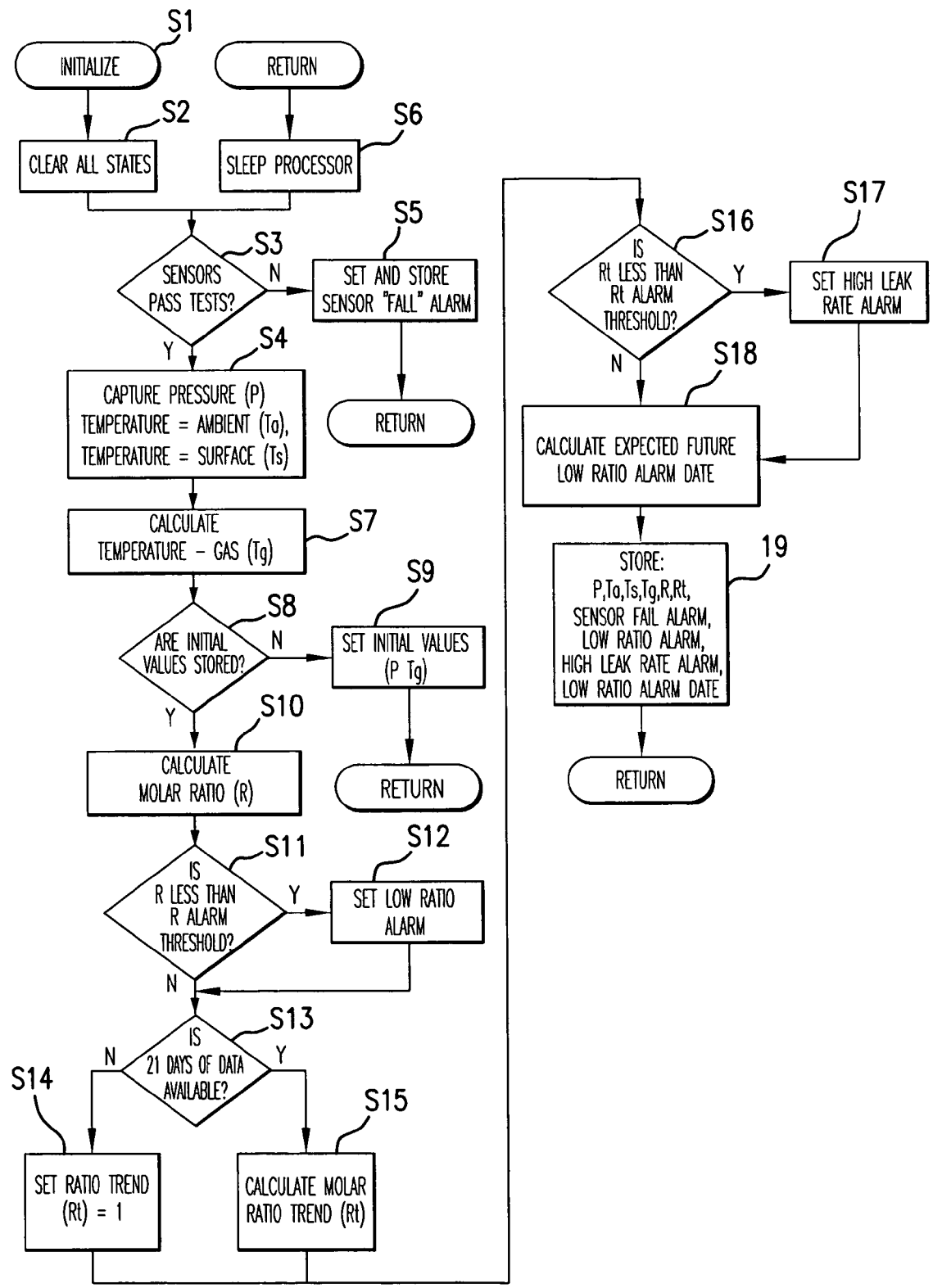
FIG. 2 shows a SF6 monitor microprocessor computer program logic flow chart used with this invention.

The SF6 microprocessor (computer) located in the gateway (30) logic flow chart is shown in FIG. 2. After initialization, at step S1, control passes to step S2 which clears all states in order to begin. Next control passes to S3 where the sensors are tested. If the sensors pass the test, control is sent to steps 4, other wise if the sensors fail the test, control is passed to step S5 where a sensor set and store of a sensor fail alarm is executed. After step S5 control is sent to return and a sleep processor S6.

At step S4 pressure, $T_{ambient}$ and $T_{surface}$ are acquired.

At step S7 the temperature of the gas is calculated according to $$(T_{ambient}+T_{surface})/2$$

At step S8 it is determined if the initial values $$P_{gas\ o} \text{ and } T_{gas\ o}$$

have been stored. If the initial values have not been stored, control passes to step S9 where the initial values are set. After initial values are set control is sent to return.

At step S10 the molar ratio is calculated. Next at step S11 it is determined if the ratio is less than a preset alarm value. If the ratio is less than the alarm value, a low ratio alarm set at step S12. If the ratio is not less than the alarm threshold then control passes to step S13 where it is determined if there is 21 days of data available. If 21 days of data are not available, then control passes to step S14 where a ratio trend Rt is set. On the other hand if 21 days of data are available, then control passes to step S15 and molar ratio trend is calculated.

At step S16 it is determined if Rt is less than an alarm threshold control passes to step S17 which sets a high leak rate alarm. If Rt is not less than a preset Rt, alarm threshold than at step S18 a calculation if a future low ratio alarm date is made. At step S19 values for P, $T_{ambient}$, $T_{surface}$, $T_{gas}$, R, Rt, sensor fail alarm, low ratio alarm, high leak alarm, and low ratio alarm data are recorded. Control then passes to return.

Figure 3:
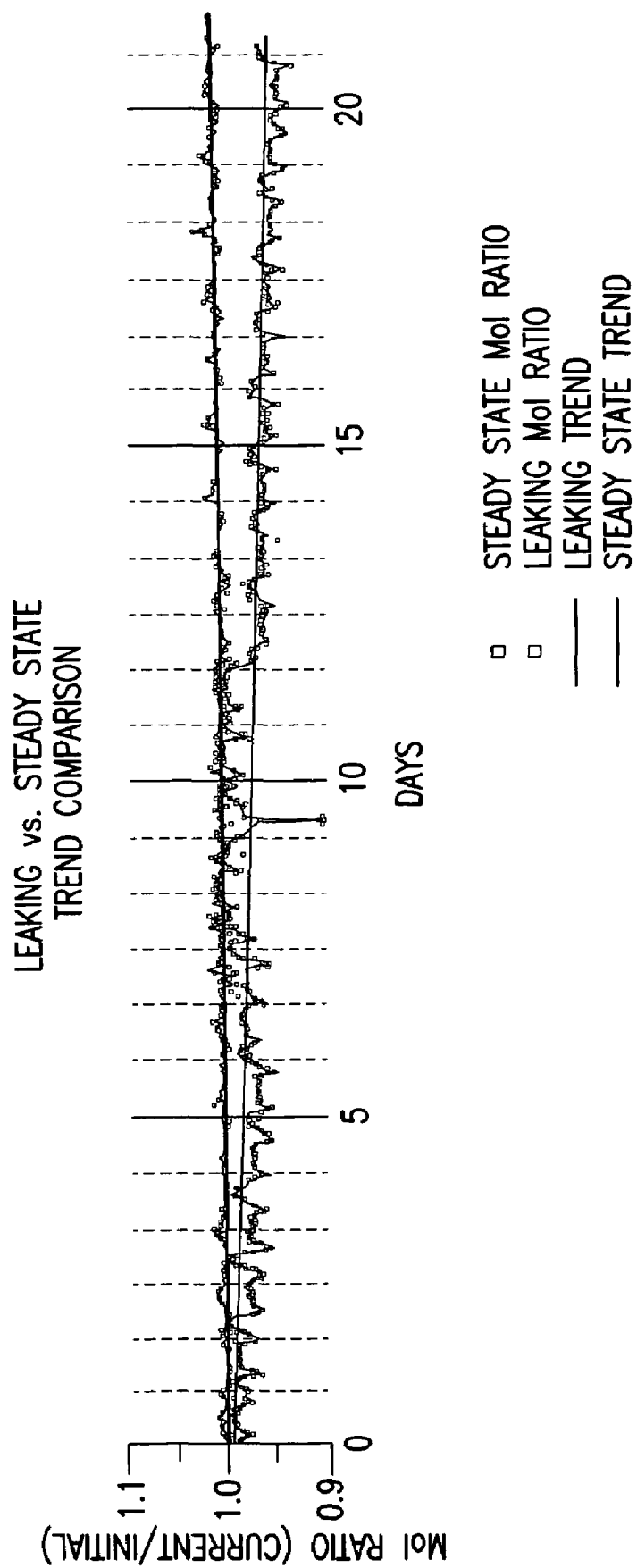
FIG. 3 shows a graph of a leaking vs steady state trend comparison for data taken over a period of 21 days.

In FIG. 3 there is shown a graph of molar ratio or the ratio of:

$$n_n/n_o \text{ which is } (P_{gas\ n}/T_{gas\ n}) \div (P_{gas\ o}/T_{gas\ o})$$

which is constant when there is no leakage. The top line shows actual data taken over a 20 day period when no leakage is present. On the other hand, the decreasing sloping line shows other measurements where leaking is occurring and the measured value of the ratio P÷T is decreasing. On the other hand if the mole ratio $$n_o/n_n$$

is used, then an increasing sloping line will indicate measurements where leaking is occurring.

The invention claimed is:

1. A method for detecting loss of SF6, also known as sulfur hexafluoride, gas from electric utility apparatus comprising the steps of:
   taking measurements at a beginning time and a later time;
   wherein taking measurements comprise the steps of:
   detecting pressure of a gas containing SF6, also know as sulfur hexafluoride, in a container which encloses an electric utility apparatus;
   detecting ambient temperature where the electric utility apparatus is located;
   detecting temperature of an outer surface of the container, and
   computing an average of the ambient temperature and the temperature of an outer surface of the container;
   computing a molar ratio using pressure and the computed average temperature measurements taken at the beginning time and the later time; and
   wherein SF6, also known as sulfur hexafluoride, gas loss from the electric utility apparatus is detected by comparing molar ratio between measurements taken at the beginning time and the later time, and
   conveying SF6, also known as sulfur hexafluoride, loss to a operator.

2. A method for detecting loss of SF6, also known as sulfur hexafluoride, gas from electric utility apparatus according to claim 1 where the molar ratio is computed as follows:

$$\text{molar ratio} = n_n/n_o$$

or $$\text{molar ratio} = n_o/n_n$$

where $n_n$ is a measurement taken at a subsequent time and $n_o$ is a measurement taken at the beginning time.

3. A method for detecting loss of SF6, also known as sulfur hexafluoride, gas from electric utility apparatus according to claim 2 wherein $$n_o = P_{gas\ o}/T_{gas\ o}$$

and $$n_n = P_{gas\ n}/T_{gas\ n}$$

where P is pressure and T is temperature.

4. A method for detecting loss of SF6, also known as sulfur hexafluoride, gas from electric utility apparatus comprising the steps of:
   taking measurements at a beginning time and a later time;
   wherein taking measurements comprise the steps of:
   detecting pressure of a gas containing SF6, also known as sulfur hexafluoride, in a container which encloses an electric utility apparatus;
   detecting ambient temperature where the electric utility apparatus is located;
   detecting temperature of an outer surface of the container, and
   computing an average of the ambient temperature and the temperature of an outer surface of the container;
   computing a molar ratio using pressure and the computed average temperature measurements taken at the beginning time and the later time; and
   wherein SF6, also known as sulfur hexafluoride, gas loss from the electric utility apparatus is detected by comparing molar ratio between measurements taken at the beginning time and the later time, and
   where the molar ratio is computed as follows:

$$\text{molar ratio} = n_n/n_o$$

or $$\text{molar ratio} = n_o/n_n$$

where $n_n$ is a measurement taken at a subsequent time and $n_o$ is a measurement taken at the beginning time and further comprising the steps of taking a plurality of measurements at different times after the beginning time and establishing a ratio trend line based upon at least two of the plurality of measurements.

5. A method for detecting loss of SF6, also known as sulfur hexafluoride, gas from electric utility apparatus comprising the steps of:
   taking measurements at a beginning time and a later time;
   wherein taking measurements comprise the steps of:
   detecting pressure of a gas containing SF6, also known as sulfur hexafluoride, in a container which encloses an electric utility apparatus;
   detecting ambient temperature where the electric utility apparatus is located;
   detecting temperature of an outer surface of the container, and
   computing an average of the ambient temperature and the temperature of an outer surface of the container;
   computing a molar ratio using pressure and the computed average temperature measurements taken at the beginning time and the later time; and
   wherein SF6, also known as sulfur hexafluoride, gas loss from the electric utility apparatus is detected by comparing molar ratio between measurements taken at the beginning time and the later time, and further comprising the steps of taking a plurality of measurements at different times after the beginning time and establishing a ratio trend line based upon at least two of the plurality of measurements.

6. A method for detecting loss of SF6, also known as sulfur hexafluoride, gas from electric utility apparatus according to claim 5 wherein the trend line is established with a least squares analysis of the molar ratio.

7. A method for detecting loss of SF6, also known as sulfur hexafluoride, gas from electric utility apparatus according to claim 5 further comprising the steps of determining if the ratio trend line is declining in value at a rate which is greater than a predetermined rate and out-putting a signal when the predetermined rate is exceeded.

8. A method for detecting loss of SF6, also known as sulfur hexafluoride, gas from electric utility apparatus according to claim 7 further comprising the step of activating a digital alarm when the predetermined rate is exceeded.

9. A method for detecting loss of SF6, also known as sulfur hexafluoride, gas from electric utility apparatus comprising the steps of:
   taking measurements at a beginning time and a later time;
   wherein taking measurements comprise the steps of:
   detecting pressure of a gas containing SF6, also known as sulfur hexafluoride, in a container which encloses an electric utility apparatus;
   detecting temperature of an outer surface of the container, and
   wherein the molar ratio is computed using measurements taken at the beginning time and the later time;
   wherein loss is determined by comparing a molar ratio at the beginning time and the later time and
   comprising the steps of taking a plurality of measurements at different times after the beginning time and establishing a ratio trend line based upon at least two measurements taken after at a plurality of times after a first measurement.

10. A method for detecting loss of SF6, also known as sulfur hexafluoride, gas from electric utility apparatus according to claim 9 further comprising the steps of determining if the ratio trend line is declining in value at a rate which is greater than a predetermined rate and out-putting a signal when the predetermined rate is exceeded.

11. A method for detecting loss of SF6, also known as sulfur hexafluoride, gas from electric utility apparatus according to claim 10 further comprising the step of activating a digital alarm when the predetermined rate is exceeded.

12. A method for detecting loss of SF6, also known as sulfur hexafluoride, gas from electric utility apparatus according to claim 9 wherein the trend line is established with a least squares analysis of the molar or density ratios.

13. A method for detecting loss of SF6, also known as sulfur hexafluoride, gas from electric utility apparatus according to claim 9 wherein the molar ratio is computed as follows:

$$\text{molar ratio} = n_n/n_o$$

or $$\text{molar ratio} = n_o/n_n$$

where $n_n$ is a measurement taken at a subsequent time and $n_o$ is a measurement taken at the beginning time.

14. A method for detecting loss of SF6, also known as sulfur hexafluoride, gas from electric utility apparatus according to claim 13 wherein $$n_o = P_{gas\,o}/T_{gas\,o}$$

and $$n_o = P_{gas\,n}/T_{gas\,n}$$

where P is pressure and T is temperature.

15. An apparatus for detecting loss of SF6, also known as sulfur hexafluoride, gas from electric utility apparatus comprising:
   a pressure detector for detecting pressure of a gas containing SF6, also known as sulfur hexafluoride, in a container which encloses an electric utility apparatus;
   a temperature detector for detecting ambient temperature where the electric utility apparatus is located;
   a temperature detector for detecting temperature of an outer surface of the container, and
   a computer which computes average temperature measurements of the ambient temperature and the temperature of an outer surface of the container, a molar ratio using pressure and the computed average temperature measurements, taken at a beginning time and a later time; and
   wherein loss is determined by comparing molar ratio between measurements taken at the beginning time and the later time.

16. An apparatus for detecting loss of SF6, also known as sulfur hexafluoride, gas from electric utility apparatus according to claim 15 wherein the a detector includes the apparatus for detecting pressure and temperature and the detector sends unprocessed data to a gateway through a transmitting antenna.

17. An apparatus for detecting loss of SF6, also known as sulfur hexafluoride, gas from electric utility apparatus according to claim 15 wherein the molar ratio is determined by the computer as follows:

$$\text{molar ratio} = n_n/n_o$$

or $$\text{molar ratio} = n_o/n_n$$

where $n_n$ is a measurement taken at a subsequent time and $n_o$ is a measurement taken at the beginning time.

18. An apparatus for detecting loss of SF6, also known as sulfur hexafluoride, gas from electric utility apparatus according to claim 17 wherein $$n_o = P_{gas\,o}/T_{gas\,o}$$

and $$n_n = P_{gas\,n}/T_{gas\,n}$$

where P is pressure and T is temperature.

* * * * *